United States Patent [19]

Maresca

[11] Patent Number: 4,757,149
[45] Date of Patent: Jul. 12, 1988

[54] SYNTHESIS OF BIS(N-SUBSTITUTED PHTHALIMIDE)ETHERS

[75] Inventor: Louis M. Maresca, Pittsfield, Mass.

[73] Assignee: General Electric Company, Pittsfield, Mass.

[21] Appl. No.: 948,045

[22] Filed: Dec. 31, 1986

[51] Int. Cl.⁴ .......................................... C07D 209/48
[52] U.S. Cl. ..................................................... 548/461
[58] Field of Search ....................................... 548/461

[56] References Cited

U.S. PATENT DOCUMENTS

| | | | |
|---|---|---|---|
| 3,879,428 | 4/1975 | Heath et al. | 60/346.3 |
| 3,933,852 | 1/1976 | Cook et al. | 260/326 N |
| 4,017,511 | 4/1977 | Williams, III | 548/461 |
| 4,054,577 | 10/1977 | Relles et al. | 548/461 |
| 4,116,980 | 9/1978 | Webb | 260/346.3 |
| 4,417,044 | 1/1983 | Parekh | 528/179 |

OTHER PUBLICATIONS

Kolesnikov G. S. et al. (1967) *Vysokomal Soyed* A9: 612–618.
*Chemical Abstracts* 94:83799g (1980), Mitsui Toatsu Chemicals.
*Chemical Abstracts* 95:42680p (1981), Mitsui Toatsu Chemicals.
*Organic Chemistry* 3rd Ed., (R. Morrison and R. Boyd); Allyn and Bacon, Inc., Boston, Mass., 1977, pp. 31–32.

Primary Examiner—Mary E. Ceperley
Attorney, Agent, or Firm—Bernard, Rothwell & Brown

[57] ABSTRACT

Bis(N-substituted phthalimide)ethers are synthesized in a one-step process by heating a compound of the formula (I):

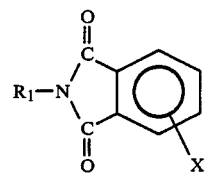

with a catalytic amount of an alkali or alkaline earth metal carbonate in a polar aprotic solvent under ether-forming conditions, and recovering the bis(N-substituted phthalimide)ether from the reaction mixture. $R_1$ is hydrogen; a monovalent organic radical selected from a lower alkyl group having from 1 to about 10 carbon atoms, preferably from 1 to about 5 carbon atoms; or an aromatic hydrocarbon radical, or halogenated derivative thereof, having from about 6 to about 20 carbon atoms. X is a leaving group.

17 Claims, No Drawings

SYNTHESIS OF BIS(N-SUBSTITUTED PHTHALIMIDE)ETHERS

TECHNICAL FIELD

This invention relates to a method of synthesizing bis(N-substituted phthalimide)ethers. These compounds are useful as intermediates in the synthesis of bis(phthalic anhydride)ethers, which are used in the synthesis of certain polyetherimides.

BACKGROUND OF THE INVENTION

The bis(N-substituted phthalimide)ethers are known intermediates used in the synthesis of certain polyetherimides. These compounds are readily converted to the corresponding bis(phthalic anhydride)ethers, by, for example, hydrolyzing with aqueous sodium hydroxide and neutralizing to form the corresponding tetracarboxylic acid, then treating the tetracarboxylic acid with glacial acetic acid and acetic anhydride to form the dianhydride. These procedures are described in general terms in U.S. Pat. Nos. 3,933,852 and 3,879,428.

The bis(phthalic anhydride)ether is useful as a monomer for the preparation of various polyetherimide homopolymers and copolymers. (See, for example, Kolesnikov, G.S., et al., *Vysokomal. Soyed.* A9: No. 3, pp. 612–618, 1967.) The dianhydride has been found particularly useful for the preparation of polyetherimide copolymers which are characterized by high heat distortion temperatures and excellent thermal stability, processability and chemical resistance.

Procedures for the synthesis of bis(phthalic anhydride)ethers generally have been complicated, multistep processes or have been characterized by low yields. For example, Kolesnikov et al. (supra) describe a multistep procedure for making bis(phthalic anhydride)ether from xylene. Other processes have suffered from slow reacton rates and/or undesirable side reactions. Additional steps may be required for removal of impurities which are produced by such side reactions, so that the desired product can be recovered from the reaction mixture in acceptably pure form for subsequent reactions. Procedures for preparing bis(phthalic anhydride)ethers from halo or nitro phthalic anhydride are described in *Chemical Abstracts*, 94:83799 g (1980) and 95:42680 p (1981). A need remains for a simple efficient synthetic-process for bis(N-substituted phthalimide)ethers, which would result in a savings of time and costs associated with the production of these compounds, and would, in turn, provide an efficient process for production of bis(phthalic anhydride)ether monomers for polyetherimide synthesis, by the reactions generally described above.

SUMMARY OF THE INVENTION

The present invention provides a method of synthesizing bis(N-substituted phthalimide)ethers, which comprises heating a compound of the formula (I):

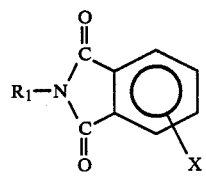

(I)

with a substantially stoichiometrically equivalent amount of an alkali or alkaline earth metal carbonate in a polar aprotic solvent under ether-forming conditions, and recovering the bis(N-substituted phthalimide)ether from the reaction mixture. $R_1$ represents hydrogen; a monovalent organic radical selected from a lower alkyl group having from 1 to about 10 carbon atoms, preferably from 1 to about 5 carbon atoms; or an aromatic hydrocarbon radical, or halogenated derivative thereof, having from about 6 to about 20 carbon atoms. X represents a leaving group, as hereinafter defined.

DETAILED DESCRIPTION OF THE INVENTION

The present invention provides an improved method for the synthesis of bis(N-substituted phthalimide)ethers. The synthesis process involves only a single step, the reaction conditions are relatively mild, the reaction rate is relatively rapid, and the product is recovered in a relatively pure, "clean" form. The method comprises heating a phthalimide compound of the formula (I):

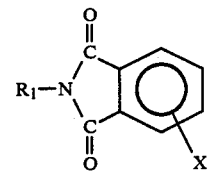

with a substantially stoichiometrically equivalent amount of an alkali or alkaline earth metal carbonate in a polar aprotic solvent under ether-forming conditions. The product may be recovered by any convenient method, such as by cooling the reaction mixture, then mixing it with water to precipitate the bis(N-substituted phthalimide)ether. A more detailed description of this process is presented below.

The formation of the bis(N-substituted phthalimide)ether may be depicted as follows:

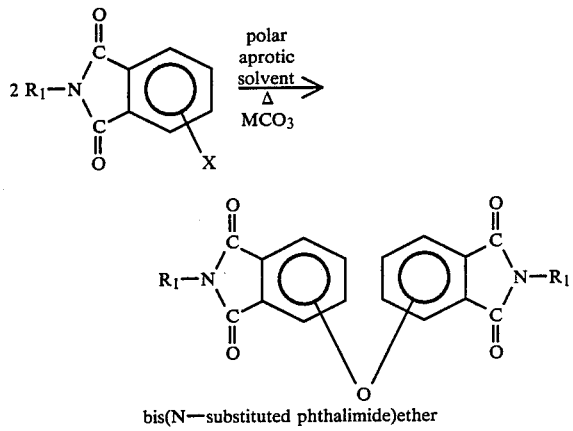

bis(N—substituted phthalimide)ether $R_1$ represents hydrogen; a monovalent organic radical selected from a lower alkyl group having from 1 to about 10 carbon atoms, preferably from 1 to about 5 carbon atoms; or an aromatic hydrocarbon radical, or halogenated derivative thereof, having from about 6 to about 20 carbon atoms. Radicals included by $R_1$ are, for example, aromatic radicals such as phenyl, tolyl, xylyl, naphthyl, chlorophenyl, and bromonaphthyl, and alkyl radicals such as methyl, ethyl, and propyl groups. A particularly preferred $R_1$ group is methyl. X represents a leaving group. As used herein, "leaving group" refers to groups which are readily displaced from the starting compound under ether-forming conditions of the reaction. Advantageously, X is a nitro group (i.e., $-NO_2$) or a halogen atom such as chloro, bromo, or fluoro, preferably fluoro. X may be bonded at the 3 or 4 positions of the benzene ring shown in formula (I).

Phthalimide compounds of formula (I) are known. (See, for example, U.S. Pat. Nos. 4,116,980; 3,933,852 and 3,879,428.) In accordance with the invention, and the definitions of the $R_1$ and X groups presented above, the compound of formula (I) may be, for example, N-phenyl-3-nitrophthalimide, N-methyl-4-nitrophthalimide, N-butyl-3-chlorophthalimide, N-propyl-4-bromophthalimide, N-methyl-4-fluorophthalimide, and many other such compounds.

In the above formula, "$MCO_3$" represents an alkali or alkaline earth metal carbonate. Preferred alkali metals include lithium, sodium, potassium, and cesium. Preferred alkaline earth metals include magnesium, calcium and barium. Particularly preferred carbonate compounds for use in the method of the present invention are sodium carbonate ($Na_2CO_3$), potassium carbonate ($K_2CO_3$), calcium carbonate ($CaCO_3$), cesium carbonate ($Cs_2CO_3$), or mixtures thereof, with potassium carbonate being most preferred.

The reaction is conducted in a polar aprotic solvent. Such solvents (which are commercially available) are generally non-acid, oxygen, sulfur and/or nitrogen-containing organic solvents, including, for example, N,N-dimethylacetamide, N-methylpyrolidinone, N,N-dimethylformamide, dimethylsulfoxide, hexamethylphosphoramide, tetramethylene sulfone (sulfolane), and the like, or mixtures thereof. Polar aprotic solvents are described in, for example, U.S. Pat. No., 4,417,044 (column 6) and *Organic Chemistry*, 3rd Ed. (R. Morrison and R. Boyd; Allyn and Bacon, Inc., Boston, 1977, pp. 31–32.) A preferred organic solvent for use in the method of the present invention is N-methylpyrrolidinone.

As used herein, "ether-forming conditions" generally include heating the reaction mixture to a temperature sufficiently high to achieve substantial conversion of the N-substituted phthalimide compound of formula I to the bis(N-substituted phthalimide)ether. Such temperature advantageously ranges from about 100° C. to about 300° C., preferably from about 150° C. to about 250° C. The reaction is conveniently conducted by heating the mixture to reflux. To avoid deleterious side reactions, the reaction mixture is advantageously maintained under an inert atmosphere and substantially anhydrous conditions. A preferred procedure involves conducting the reaction under a dry nitrogen atmosphere.

The alkali or alkaline earth metal carbonate is employed in the reaction mixture in an amount which is substantially stoichiometrically equivalent to the amount of the compound of formula (I). Such amount may vary considerably, depending upon the concentration of the reactant of formula (I) and the reaction temperature. In general, the molar ratio of the alkali or alkaline earth metal carbonate to the N-substituted phthalimide compound of formula (I) ranges from about 0.25:1 to about 0.75:1, preferably from about 0.40:1 to about 0.60:1. Greater amounts of the carbonate do not significantly improve the reaction yield or efficiency and may interfere with recovery procedures, whereas lower concentrations may not provide the desired rate of reaction between the compound of formula (I) and the alkali or alkaline earth metal carbonate.

The concentration of the reactant of formula (I) in the aprotic, polar solvent may also vary over a fairly wide range. The solvent acts as the medium for the reaction, therefore the concentrations of the reactant and the product advantageously do not exceed the solubilities of those components at the temperatures employed. On the other hand, the reactant of formula (I) preferably is added to the reaction mixture at high enough concentrations so that the reaction proceeds at a satisfactory rate. In general, the initial concentration of the N-substituted phthalimide compound of formula (I) ranges from about 0.01 to about 1.0 gram, preferably from about 0.05 to about 0.5 gram per milliliter of the polar, aprotic solvent.

The product may be recovered from the reaction mixture by any suitable means. Suitable known recovery methods include, but are not limited to, evaporation of the solvent to leave the product as a solid, followed by washing of the product with water; coagulation of the product with water or methanol to precipitate it, recovery of the precipitate, e.g., by centrifugation or filtration, then washing the precipitate with water or alcohol; or distillation. In one embodiment of the invention, the reaction mixture is cooled to between about ambient temperatures and 100° C., and then poured into water, whereupon the bis(N-substituted phthalimide)ether product precipitates. The volume of the water is preferably between about 1 and about 10 times the volume of the reaction mixture. Preferrably, distilled water is used to minimize introduction of impurities into the reaction mixture.

The precipitated product may be collected by any suitable means, including, but not limited to, known methods of filtration and centrifugation. If desired, the product may be further purified by washing, e.g., with water and alcohol. The product then may be dried by conventional means, such as in a vacuum oven. Numerous other recovery procedures will occur to those skilled in the art, and the invention is not limited to any particular recovery procedure.

The method of this invention provides a simple one-step procedure for preparing bis(N-substituted phthalimide)ethers. The method results in a relatively pure product that can be readily recovered in good yields. The bis(N-substituted phthalimide)ethers may be converted to the corresponding bis(phthalic anhydride)ethers, which, in turn, are useful in polyetherimide synthesis by known procedures, as described above.

The examples provided below are presented to illustrate certain embodiments of the invention disclosed herein, and are not to be construed as limiting the scope thereof.

EXAMPLE 1

Preparation of 4,4'-Bis(N-methylphthalimide)Ether

A slurry of 309.0 g (1.50 moles) of N-methyl-4-nitrophthalimide (a compound of formula I in which $R_1$ is methyl and X is a nitro group) and 114.0 g (0.825 moles) of potassium carbonate in 1500 ml of N-methylpyrrolidinone was heated to 160°–165° C. under a nitrogen atmosphere. After maintaining this temperature for 3 hours, the reaction mixture was cooled to about 50° C. and then poured into 6000 ml of water. The resulting precipitate was collected by vacuum filtration, washed sequentially with water (1500 mls) and isopropanol (1500 mls) and then dried in a vacuum oven at 100° C. overnight. A 55% yield (138.5 g) of the desired product, i.e., 4,4'-bis(N-methylphthalimide)ether was obtained.

EXAMPLE 2

Preparation of 4,4'-Bis(N-methylphthalimide)Ether

A slurry of 10.30 g (0.05 moles) of N-methyl-4-nitrophthalimide, 2.51g (0.0238 moles) of sodium carbonate, 0.17 g (0.0013 moles) of potassium carbonate in 100 ml of N-methylpyrrolidinone and 25 ml of toluene was heated to reflux (160°-165° C.) for 1.5 hours. After cooling to 50° C., the mixture was poured into 300 ml of water. The precipitate was collected by vacuum filtration, washed sequentially with water (500 ml) and isopropanol (500 ml) and then dried in a vacuum oven at 100° C. overnight. A 65% yield (5.46 g) of 4,4'-bis(N-methylphthalimide)ether was obtained.

EXAMPLE 3

Preparation of 4,4'-Bis(N-methylphthalimide)Ether

A slurry of 10.30 g (0.05 moles) of N-methyl-4-nitrophthalimide and 3.8 g (0.0275 moles) of potassium carbonate in 100 ml of N,N-dimethylacetamide was heated under a nitrogen atmosphere to reflux (160° C.). After 2 hours at reflux the mixture was cooled to about 50° C. and poured into 500 ml of water. The precipitate was collected by filtration, washed sequentially with water (500 ml) and isopropanol (500 ml) and then dried in a vacuum oven at 100° C. overnight. A 46% yield of 4,4'-bis(N-methylphthalimide)ether was obtained.

What is claimed is:

1. A method for synthesizing bis(N-substituted phthalimide)ether, comprising heating a reaction mixture consisting essentially of a compound of formula

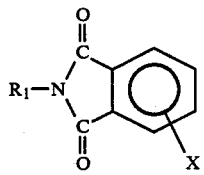

and an essentially stoichiometrically equivalent amount of an alkali or alkaline earth metal carbonate in a polar aprotic solvent under ether-forming conditions, and recovering a bis(N-substituted phthalimide)ether of the formula

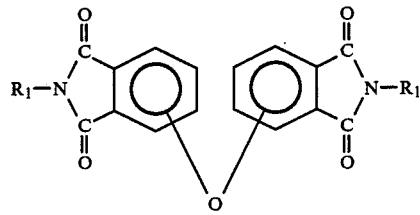

from the reaction mixture, wherein $R_1$ is selected from the group consisting of hydrogen; a monovalent organic radical selected from a lower alkyl group having from 1 to about 10 carbon atoms; and an aromatic hydrocarbon radical, or halogenated derivative thereof, having from about 6 to about 20 carbon atoms; and X is a leaving group.

2. The method of claim 1, wherein $R_1$ is lower alkyl of from 1 to about 5 carbon atoms and X is a nitro group or a halogen atom.

3. The method of claim 2, wherein X is nitro, fluoro, chloro or bromo.

4. The method of claim 2 or 3, wherein $R_1$ is methyl.

5. The method of claim 1, wherein said alkali or alkaline earth metal carbonate is selected from the group consisting of lithium carbonate, sodium carbonate, potassium carbonate, cesium carbonate, magnesium carbonate, calcium carbonate, barium carbonate and mixtures thereof.

6. The method of claim 5 wherein said alkali or alkaline earth metal carbonate is selected from the group consisting of sodium carbonate, potassium carbonate, calcium carbonate, cesium carbonate and mixtures thereof.

7. The method of claim 1 wherein said polar aprotic solvent is selected from the group consisting of N,N-dimethylacetamide, N-methylpyrrolidinone, N,N-dimethylformamide, dimethylsulfoxide, hexamethylphosphoramide, tetramethylene sulfone, and mixtures thereof.

8. The method of claim 7, wherein said polar aprotic solvent is N-methylpyrrolidinone.

9. The method of claim 1, wherein said etherforming conditions comprise heating the reaction mixture to a temperature of from about 100° C. to about 300° C. under an inert atmosphere and under substantially anhydrous conditions.

10. The method of claim 9, wherein said inert atmosphere is a nitrogen atmosphere.

11. The method of claim 9, wherein said reaction mixture is heated to from about 150° C. to about 250° C.

12. The method of claim 1, wherein the molar ratio of the alkali or alkaline earth metal carbonate to the N-substituted phthalimide compound of formula (I) is from about 0.25:1 to about 0.75:1.

13. The method of claim 12, wherein said molar ratio is from about 0.40:1 to about 0.60:1.

14. The method of claim 1, wherein said bis(N-substituted phthalimide)ether is recovered by cooling said reaction mixture and mixing said reaction mixture with water to precipitate said bis(N-substituted phthalimide)ether.

15. The method of claim 14, wherein said reaction mixture is mixed with from about 1 to about 10 volumes of distilled water.

16. The method of claim 14 wherein said precipitated bis(N-substituted phthalimide)ether is collected by centrifugation or filtration.

17. The method of claim 16 wherein said precipitated bis(N-substituted phthalimide)ether is collected by filtration, washed and then dried.

* * * * *